United States Patent [19]

Imai

[11] Patent Number: 4,487,984

[45] Date of Patent: Dec. 11, 1984

[54] SYNTHESIS OF ALKYLAROMATIC COMPOUNDS

[75] Inventor: Tamotsu Imai, Mount Prospect, Ill.

[73] Assignee: UOP Inc., Des Plaines, Ill.

[21] Appl. No.: 584,375

[22] Filed: Feb. 28, 1984

[51] Int. Cl.$^3$ ............................................... C07C 1/00
[52] U.S. Cl. ..................................... 585/454; 585/467
[58] Field of Search ................................. 585/454, 467

[56] References Cited

U.S. PATENT DOCUMENTS

| | | | |
|---|---|---|---|
| 3,718,704 | 2/1973 | Chapman et al. | 585/454 |
| 4,086,289 | 4/1978 | Seitzer | 585/454 |
| 4,409,412 | 10/1983 | Haag et al. | 585/454 |

*Primary Examiner*—Curtis R. Davis
*Attorney, Agent, or Firm*—William H. Page, II; Raymond H. Nelson

[57] ABSTRACT

Alkylaromatic compounds may be synthesized by reacting an aromatic compound with a mixture of carbon monoxide and hydrogen at alkylation conditions in the presence of a dual-function catalyst. The catalyst system will comprise (1) a composite of oxides of copper, zinc and aluminum or chromium, and (2) an aluminosilicate which may be either in crystalline or amorphous form.

16 Claims, No Drawings

SYNTHESIS OF ALKYLAROMATIC COMPOUNDS

BACKGROUND OF THE INVENTION

Alkylaromatic compounds and particularly alkylaromatic hydrocarbons will find a wide variety of uses in the chemical field. For example, toluene which may be obtained by the catalytically reforming of petroleum, by fractional distillation of coal tar light oil, by extraction from coal gas, etc. is used in aviation gasoline, as well as high octane blending stock, as a solvent, in paints and coatings, rubber cement, in medicines, dyes, perfumes or as an intermediate in the preparation of polyurethane resins, explosives, detergents, etc. Likewise, the isomeric xylenes also find a wide variety of uses. For example, o-xylene may be used in vitamin and pharmaceutical syntheses, in dyes, insecticides, in the manufacture of phthalic anhydride; m-xylene may be used as a solvent, as an intermediate for dyes and organic syntheses; p-xylene is used in the synthesis of terephthalic acid which is an intermediate for the production of synthetic resins and fibers such as Dacron, Mylar, etc., while mixtures of the isomeric xylenes may be used in aviation gasoline, protective coatings, as a solvent for alkyl resins, lacquers, enamels, rubber cements, etc. Other alkylaromatic hydrocarbons which are also useful in commercial chemical processes include cumene (isopropylbenzene) which is used as an additive to aviation gasoline or in the production of other chemicals such as phenol, acetone, etc., and ethylbenzene which is used as a solvent and diluent or as an intermediate in the production of styrene.

As hereinbefore set forth, the simple alkylaromatics such as toluene and the xylenes are obtained from petroleum or gas. I have now discovered that alkylaromatic compounds may be synthesized from an aromatic compound or other alkylaromatic compounds by reacting the aromatic compound with a syngas containing carbon monoxide and hydrogen utilizing a dual-catalyst or dual-function-catalyst system. This dual-catalyst will be hereinafter further described in greater detail.

SUMMARY OF THE INVENTION

This invention relates to a process for the synthesis of alkylaromatic compounds. More particularly, the invention is concerned with a process for the synthesis of alkylaromatic compounds by reacting an aromatic compound of the type hereinafter set forth in greater detail with a mixture of gases containing, as predominant components thereof, carbon monoxide and hydrogen.

It is therefore an object of this invention to provide a process for the synthesis of an alkylaromatic compound.

A further object of this invention is found in a process for the synthesis of alkylaromatc hydrocarbons by reacting an aromatic hydrocarbon with a mixture of gases including carbon monoxide and hydrogen in the presence of certain catalytic systems.

In one aspect an embodiment of this invention resides in a process for the synthesis of an alkylaromatic compound which comprises reacting an aromatic compound with a mixture of hydrogen and carbon monoxide at reaction conditions in the presence of a catalyst system comprising (1) a composite of oxides of copper, zinc and aluminum or chormium and (2) an aluminosilicate, and recovering the resultant alkylaromatic compound.

A specific embodiment of this invention is found in a process for the synthesis of an alkylaromatic compound which comprises reacting benzene with hydrogen and carbon monoxide at a temperature in the range of from about 200° to about 400° C. and a pressure in the range of from about 1 to about 100 atmospheres in the presence of a catalyst system comprising an admixture of a composite of oxides of copper, zinc and aluminum and a crystalline aluminosilicate in which the ratio of aluminum to silicon is greater than 2:1, and recovering the resultant mixture comprising toluene, ethylbenzene, p-xylene, m-xylene, o-xylene and cumene.

Other objects and embodiments will be found in the following further detailed description of the invention.

DETAILED DESCRIPTION OF THE INVENTION

As hereinbefore set forth, the present invention is concerned with a process for the synthesis of alkylaromatic compounds in which an aromatic compound is alkylated utilizing, as the alkylating agent thereof, a mixture of carbon monoxide and hydrogen. The alkylating agent which is used to produce the desired compound will comprise a mixture of gases and preferably a mixture of carbon monoxide and hydrogen which is commercially known as synthesis gas. The hydrogen and carbon monoxide which are present in this mixture of gases may be in various proportions, the preferred proportions for the present invention being that in which the mole ratio of hydrogen to carbon monoxide is in a range of from about 1:1 up to about 5:1 moles of hydrogen per mole of carbon monoxide. In addition to the carbon monoxide and hydrogen, carbon dioxide may be present in a range of from 0.01:1 to 1:1 moles of carbon dioxide per mole of carbon monoxide, as well as other gases which may be present in relatively small amounts, said gases including methane, oxygen and nitrogen. The synthesis gas which is used as the alkylating agent may be obtained from any source such as by the high temperature action of steam on carbon or natural gas, by the partial oxidation of natural gas, etc.

The aromatic compounds which may be alkylated with the aforesaid synthesis gas may include aromatic hydrocarbons such as benzene, toluene, ethylbenzene, cumene, naphthalene, chrysene, anthracene, phenanthrene or an aromatic compound which possesses a substituent such as phenol, cresol, etc.

Reaction conditions which are employed to effect the alkylation of the aromatic compound with the synthesis gas will include elevated temperatures and pressures, said temperatures being in a range of from about 200° up to about 400° C. or more and pressures which may range from about 1 to about 100 atmospheres. In the preferred embodiment of the invention the pressures which are utilized to effect the alkylation reaction will comprise the autogenous pressures of the synthesis gas. However, it is also contemplated within the scope of this invention that the synthesis gas may afford only a partial pressure, the remaining portion of the desired operating pressure being supplied by the introduction of a substantially inert gas such as nitrogen, helium, argon, etc. into the reaction zone.

The catalyst system which is used in the synthesis of alkylaromatic compounds comprises a composite of oxides of copper, zinc, and aluminum or chromium as one component and as a second component, an aluminosilicate of the type hereinafter set forth in greater detail. The catalyst system may comprise either a dual-catalyst system or a dual-function-catalyst. As was previously mentioned, the one component comprises a composite of oxides of copper, zinc and aluminum or chromium. This composite may be prepared by coprecipitating soluble salts of copper, zinc and aluminum or chromium followed by a neutralization to precipitate the desired salts. Examples of soluble salts of the metals which may be employed will include aluminum chloride, aluminum nitrate, chromic acetate, chromic nitrate, chromic sulfate, cuprous chloride, cupric chloride, cuprous nitrate, cupric nitrate, zinc chloride, zinc nitrate, zinc permanganate, zinc sulfate, etc. It is to be understood that the aforementioned soluble salts are only representative of the salts which may be employed to prepare the desired composite and that the present invention is not necessarily limited thereto.

The aforesaid salts are admixed in a suitable solvent such as water and after dissolving the salts which are present in an amount so that the finished catalyst system will contain a predetermined amount of metals in the form of oxides, the solution is neutralized by the addition of a neutralizing agent such as sodium hydroxide, potassium hydroxide, lithium hydroxide, ammonium hydroxide, sodium carbonate, potassium carbonate, lithium carbonate, ammonium carbonate, etc. to a pH of about 7, the neutralization of the solution acting to promote the precipitation of the compounds. After formation of the precipitate has occurred, it is then allowed to age for a predetermined period of time which may range from about 0.1 to about 1 hour or more at an elevated temperature of from about 50° to about 75° C. or higher. Upon completion of the aging period, the precipitate is then rinsed with deionized water to remove the alkaline material and dried, preferably at a temperature slightly in excess of 100° C., i.e., 110° C. The precipitate may then be sized to a desired mesh which may range from about 20 to about 60 mesh or, if so desired, the precipitate may then be calcined at an elevated temperature in the range of from about 250° C. to about 300° C. in nitrogen or air for a period of time which may range from about 2 to about 4 hours. If so desired, an additional compound may be added to the composite. The precipitate, after drying and sizing may be impregnated with a soluble salt of a Group IA metal or boron by any method known in the art so that the final oxide component will contain from about 0.01 to about 5% by weight of the metal or boron. Examples of salts which may be employed for the impregnation will include boric acid, sodium nitrate, sodium carbonate, sodium formate, sodium acetate, sodium hydroxide, potassium nitrate, potassium carbonate, potassium formate, potassium acetate, potassium hydroxide, the nitrates, carbonates, formates, acetates and hydroxides of lithium, cesium and rubidium, etc. Alternatively, the addition of the Group IA metal or boron may also be accomplished by a coprecipitation technique which is employed during the precipitation of the copper, zinc and aluminum or chromium salts.

The second component of the dual-catalyst system will comprise an aluminosilicate which may be either in crystalline or amorphous form, the preferred aluminosilicate containing a silicon-to-aluminum ratio greater than about 2:1. In one embodiment of the invention the compounds will comprise zeolitic crystalline aluminosilicates which may occur both naturally or which may be synthesized. In hydrated form the crystalline aluminosilicates generally encompass those zeolites represented by the Formula 1 below:

$$M_{2/n}O:Al_2O_3 \cdot wSiO_2 \cdot yH_2O \qquad \text{Formula 1}$$

where "M" is a cation which balances the electrovalence of the aluminum-centered tetrahedra and which is generally referred to as an exchangeable cationic site, "n" represents the valence of the cation, "w" represents the moles of $SiO_2$, and "y" represents the moles of water. The generalized cation "M" may be monovalent, divalent or trivalent or mixtures thereof.

Types of well-known crystalline aluminosilicates include zeolites in either the X or Y form. The X zeolite in the hydrated or partially hydrated form can be represented in terms of mole oxides as shown in Formula 2 below:

$$(0.9\pm0.2)M_{2/n}O:Al_2O_3:(2.50\pm0.5)SiO_2 \cdot yH_2O \qquad \text{Formula 2}$$

where "M" represents at least one cation having a valence of not more than 4, "n" represents the valence of "M", and "y" is a value up to about 9 depending upon the identity of "M" and the degree of hydration of the crystal. As noted from Formula 2 the $SiO_2/Al_2O_3$ mole ratio of X zeolite is 2.5±0.5. The cation "M" may be one or more of a number of cations such as a hydrogen cation, an alkali metal cation, or an alkaline earth cation, or other selected cations, and is generally referred to as an exchangeable cationic site. As the X zeolite is initially prepared, the cation "M" is usually predominately sodium, that is, the major cation at the exchangeable cationic sites is sodium, and the zeolite is therefore referred to as a sodium-X zeolite. Depending upon the purity of the reactants used to make the zeolite, other cations mentioned above may be present, however, as impurities. The Y zeolite in the hydrated or partially hydrated form can be similarly represented in terms of mole oxides as in Formula 3 below:

$$(0.9\pm0.2)M_{2/n}O:Al_2O_3 \cdot wSiO_2 \cdot yH_2O \qquad \text{Formula 3}$$

where "M" is at least one cation having a valence not more than 4, "n" represents the valence of "M", "w" is a value greater than about 3 up to about 6, and "y" is a value up to about 9 depending upon the identity of "M" and the degree of hydration of the crystal. The $SiO_2/Al_2O_3$ mole ratio of Y zeolites can thus be from about 3 to about 6. Like the X zeolite, the cation "M" may be one or more of a variety of cations but, as the Y zeolite is initially prepared, the cation "M" is also usually predominately sodium. A Y zeolite containing predominately sodium cations at the exchangeable cationic sites is therefore referred to as a sodium-Y zeolite.

Another type of aluminosilicate which may be used comprises the pentasil family of zeolites which can also be identified in terms of mole ratios of oxides as follows:

$$0.9\pm0.2M_{2/n}O:Al_2O_3:YSiO_2:zH_2O$$

where M is a cation, n is the valence of that cation, Y is at least 5, and z is from 0 to 40. In a preferred synthesized form, the zeolite has a formula, in terms of mole ratios of oxides, as follows:

$$0.9\pm0.2M_{2/n}O:Al_2O_3:5-100\ SiO_2:zH_2O$$

and M is selected from the group consisting of a mixture of alkali metal cations, especially sodium, and tetraalkylammonium cations, the alkyl groups of which preferably contain 2-5 carbon atoms.

Members of the pentasil family of zeolites possess a definite distinguishing crystalline structure whose X-ray diffraction pattern shows the following significant lines:

TABLE 1

| Interplanar Spacing d(A) | Relative Intensity |
|---|---|
| 11.2 ± 0.2 | 60–100 |
| 10.1 ± 0.2 | 60–100 |
| 6.73 ± 0.14 | 0–20 |
| 4.63 ± 0.08 | 0–20 |
| 3.86 ± 0.07 | 40–60 |
| 3.72 ± 0.07 | 20–60 |
| 2.01 ± 0.02 | 0–20 |

These values as well as all other X-ray data are determined by standard techniques.

In Table 1 the relative intensities are given as relative values. It should be understood that this X-ray diffraction pattern is characteristic of all the species of pentasil family zeolite compositions. Ion exchange of the sodium ion with cations reveals substantially the same pattern with some minor shifts in interplanar spacing and variation in relative intensity. Other minor variations can occur depending on the silicon to aluminum ratio of the particular sample as well as if it had been subjected to thermal treatment. Ammonium is a preferred cation for ion exchange.

The two components of the catalyst system, namely the oxides of copper, zinc and aluminum or chromium being one component while the other component comprises the cryatalline or amorphous silicate, may be used as a dual-function catalyst, that is, the two catalysts may be loaded separately in the reactor in multilayers or beds or in a mixed layer. Alternatively, the dual-function catalyst may be prepared in various procedures such as by grinding the two catalysts into relatively fine particles following which the particles are thoroughly admixed followed by formation of pellets or extruding the admixture. Another method of preparing the dual-function catalyst would be to admix the precipitated oxides with the aluminosilicate and extrude the resultant mass. In the preferred embodiment of the invention the copper which is present in the catalyst system will be in a range of from about 10% to about 80%, the zinc in an amount in the range of 5% to about 80% and the aluminum or chromium in an amount in the range of about 1% to about 80%.

The process which involves the synthesis of alkyl aromatics from aromatic compounds, carbon monoxide and hydrogen may be effected in any suitable manner and may comprise either a batch or continuous type operation. For example, when a batch type operation is employed, the aromatic compound which is to undergo alkylation is placed in an appropriate pressure-resistant apparatus such as an autoclave of the rotating, mixing or stirring type along with the dual-function catalyst. The autoclave is sealed and a mixture of hydrogen and carbon monoxide along with carbon dioxide, if so desired, is charged to the atuoclave until the desired operating pressure within the range hereinbefore specified is attained. Following this, the autoclave is heated to the desired operating temperature and the alkylation reaction is allowed to proceed for a predetermined period of time which may range from about 0.5 up to about 10 hours or more in duration. Upon completion of the reaction period, heating is discontinued and after the autoclave has returned to room temperature, any excess pressure which is still present is discharged and the autoclave is opened. The reaction mixture is recovered from the autoclave, separated from the catalyst by conventional means such as filtration, decantation, centrifugation, etc. and subjected to fractional distillation, usually under reduced pressure, whereby the various alkylaromatics which have been formed during the reaction are separated and recovered.

Alternatively, the alkylation of the aromatic compound with the gaseous mixture may be effected in a continuous manner of operation. When such a type of operation is performed, the aromatic compound which is to undergo alkylation and the gaseous mixture of hydrogen and carbon monoxide which forms the alkylating agent are continuously charged to a reactor containing the catalyst system and which is maintained at the proper operating conditions of temperature and pressure. After passage of the reaction components through the reactor for a predetermined period of time, the reactant effluent is continuously withdrawn therefrom and subjected to conventional means of separation whereby the alkylaromatic components comprising the reaction products are separated from any unreacted aromatic compounds, and recovered, the latter being recycled back to the reactor to form a portion of the feedstock.

Due to the nature of the catalyst system, various modes of continuous operation may be employed to effect the alkylation reaction. For example, the catalyst system may be positioned in the reactor as a fixed bed, either in multilayers of such components of the catalyst system or as a single fixed bed of the dual-function catalyst which comprises both components of the system as a single entity. The aromatic compound which is to undergo alkylation and the alkylating agent are continuously passed through the bed of catalyst in either an upward or downward flow and the reactor effluent is continuously recovered. Another method of effecting the continuous alkylation operation comprises the moving bed type in which the catalyst system either in multilayers or as a single dual-function catalyst and the reaction components are passed through the reactor either concurrently or countercurrently to each other. A third type of continuous type of operation which may be employed comprises the slurry type of operation in which the catalyst system in the form of a dual-catalyst or a dual-function-catalyst may be admitted to the reactor as a slurry in the aromatic compound which is to undergo alkylation. It is to be understood that regardless of the type of continuous operation which is employed, the separation of the reaction product from any unreacted aromatic compound is effected in a manner previously described, the desired product being recovered while the aforesaid unreacted aromatic compound is recycled back to the reactor.

Examples of alkylaromatic compounds which may be obtained by the alkylation of the present invention will include, but not be limited to, toluene, ethylbenzene, o-xylene, m-xylene, p-xylene, n-propylbenzene, isopropylbenzene (cumene), sec-butylbenzene, o-ethyltoluene, m-ethyltoluene, p-ethyltoluene, 1,3,5-trimethylbenzene, 1,2,4-trimethylbenzene, etc.

The following examples are given for purposes of illustrating the alkylation process of the present invention. However, it is to be understood that these examples are merely illustrative in nature and that the present process is not necessarily limited thereto.

EXAMPLE I

A catalyst system which was used in the synthesis of alkylaromatic compounds was prepared by dissolving 1580.4 grams of cupric nitrate, 681.8 grams of aluminum nitrate and 657.1 grams of zinc nitrate in 6 liters of deionized water. The mixture was stirred and heated to a temperature of 65° C. Following this, 1270 grams of sodium carbonate was dissolved in 8 liters of deionized water which was also heated to a temperature of 65° C. The two solutions were then admixed by addition of the solutions to a vessel containing 9 liters of hot deionized water. The precipitate formed after the addition which occurred at a pH of 5.9. Further neutralization was accomplished by adding an additional amount of sodium carbonate and the precipitate was aged for a period of 20 minutes accompanied by continuous stirring. After aging, the precipitate was filtered and recovered.

The precipitate was then dried for a period of 12 hours at a temperature of 110° C. and sized to 20–60 mesh. The paticles were then calcined in a nitrogen atmosphere at a temperature of 260° C. for a period of 4 hours and further sized to about 40 mesh.

The second component of the dual-function catalyst was prepared by admixing an aluminosilicate in powder form with a 33 wt. % solution of aluminum phosphate. The aluminosilicate had a silicon-to-aluminum ratio of 20:1 and an ABD of 0.26 g/cc. The solution was oil dropped and after recovery of the particles, was calcined at a temperature of 350° C. in a nitrogen atmosphere which contained 2% oxygen for a period of 2 hours. The temperature of the calcination was increased to a temperature of 550° C. and maintained thereat for an additional period of 18 hours. At the end of the 18 hour period, the calcining atmosphere was changed to air for an additional period of 2 hours. The calcined material was then steamed at a temperature of 600° C. for 2 hours following which the zeolite was allowed to return to room temperature and sized to 20–40 mesh.

The zeolite component of the catalyst system and the mixed oxide component of the system were mixed in a 1:1 ratio and loaded into a reactor. The catalyst was then reduced by passing an atmosphere containing 98% nitrogen and 2% hydrogen over the catalyst at a rate of 22 scfm at a temperature of 220° C. for a period of 1 hour. The alkylation of an aromatic compound was accomplished by passing a mixture of benzene and synthesis gas over the catalyst for a period of 2 hours while maintaining a reaction temperature of 340° C. and a pressure of 450 psig. The molar feed ratio of the benzene and synthesis gas was 0.5:1:2.6:0.24 moles of benzene per mole of carbon monoxide per mole of hydrogen per mole of carbon dioxide, the addition of the reactants being effected at a LHSV based on the benzene of 1.6.

Analysis of the product showed that there had been a 29% conversion of the benzene and a 25% conversion of the carbon monoxide. Alkylaromatic hydrocarbons whihc were formed in the product are set forth in Table I below:

TABLE I

| Product | Selectivity, Mole % |
| --- | --- |
| toluene | 54.4 |
| ethylbenzene | 8.4 |
| p-xylene | 8.4 |
| m-xylene | 7.1 |
| o-xylene & cumene | 6.2 |

TABLE I-continued

| Product | Selectivity, Mole % |
| --- | --- |
| n-propylbenzene | 6.0 |
| p-ethyltoluene | 1.5 |
| m-ethyltoluene | 1.9 |
| o-ethyltoluene | 1.1 |
| 1,3,5-trimethylbenzene | 0.1 |
| 1,2,4-trimethylbenzene | 1.6 |
| heavies | 3.3 |

It is therefore readily apparent from the above Table that alkylaromatic hydrocarbons were formed by the alkylation of an aromatic compound such as benzene with a synthesis gas in the presence of the dual-catalyst system employed in the reaction.

EXAMPLE II

The oxide composite component of a catalyst system was prepared in a manner similar to that set forth in Example I above; 75 grams of the composite comprising a mixture of oxides of copper, zinc and aluminum which had been dried at 110° C. and sized to 20–60 mesh were impregnated with a methanol solution containing 0.78 gram of boric acid. The impregnated particles were cold-rolled for a period of 15 minutes at atmospheric pressure and then dried at a temperature of 40° C. under a reduced pressure ranging from 10 to 300 mm of mercury, calcined at a temperature of 260° C. in a flowing air atmosphere for a period of four hours and screened to 20–40 mesh. Analysis of this component disclosed that it contained 41.5 wt. % copper, 14.1 wt. % zinc and 5.0 wt. % aluminum.

The second component of the catalyst, which comprised an alumina-silicate in powder form prepared according to the method set forth in Example I above, was admixed with the oxide component in a 1:1 volume ratio, loaded into a reactor and reduced by treatment with a gaseous mixture containing 2% hydrogen and 98% nitrogen at a temperature of 220° C. for a period of about 16 hours.

The alkylation of an alkylaromatic compound was effected by passing a mixture of toluene and synthesis gas over the catalyst for a period of two hours, while maintaining a reaction temperature of 320° C. and a pressure of 750 psig, at a LHSV, based on the toluene, of 4.2 The molar feed ratio of the toluene and synthesis gas was 1.1:1.0:2.6:0.24 moles of toluene per mole of carbon monoxide per mole of hydrogen per mole of carbon dioxide.

Analysis of the product disclosed a 17% conversion of the toluene and a 24% conversion of cabon monoxide and carbon dioxide. Alkylaromatic hydrocarbons which were formed in the product are set forth in Table II below:

TABLE II

| Product | Selectivity, mole % |
| --- | --- |
| $C_1$–$C_4$ hydrocarbons | 8.2 |
| benzene | 5.9 |
| ethylbenzene | 0.6 |
| p-xylene | 24.3 |
| m-xylene | 30.5 |
| o-xylene | 15.4 |
| p-ethyltoluene | 2.8 |
| m-ethyltoluene | 4.4 |
| o-ethyltoluene | 0.2 |
| trimethylbenzene | 7.0 |

The above Table shows that alkylaromatic hydrocarbons were formed by the alkylation of toluene with a synthesis gas in the presence of a dual-catalyst system.

EXAMPLE III

In a manner similar to that set forth in Example I above, one component of a dual-function-catalyst system may be prepared by dissolving cupric nitrate, chromic nitrate and zinc nitrate in deionized water. After stirring the mixture and heating to a temperature of about 65° C., the solution may be neutralized by the addition of a sodium carbonate solution. The precipitate may be allowed to age for a period of about 20 minutes following which the solution may be filtered and the precipitate recovered. The precipitate comprising a mixture of oxides of copper, zinc and chromium may then be dried at a temperature of about 110° C. and thereafter calcined in a nitrogen atmosphere at a temperature of about 260° C. Following the calcination the particles may then be sized to a desired dimension such as 100 mesh.

The second component of the catalyst system comprising an aluminosilicate may be prepared by admixing an aluminosilicate in powdered form, said aluminosilicate having a silicon-to-aluminum ratio greater than 10, with the mixed oxide component and an aqueous silica sol. The resulting mixture may then be extrudated, dried and calcined at elevated temperatures ranging from about 200° to about 650° C. for varying periods of time in various atmospheres such as nitrogen, air and steam. At the end of the calcination period, the extrudate may then be sized to a desired dimension and recovered.

The dual-function-catalyst system may be placed in a suitable reactor for the alkylation of an aromatic compound. The desired alkylation reaction may be effected by charging a mixture of ethylbenzene and synthesis gas which is primarily a mixture of carbon monoxide and hydrogen to the reactor at a LHSV, based on the ethylbenzene, in a range of from about 1 to about 10 while maintaining the reactor at a temperature of about 350° C. and a pressure of about 400 psig. Following passage of the reaction mixture through the catalyst bed, the product which may contain a mixture of o-ethyltoluene, m-ethyltoluene, p-ethyltoluene, o-isopropylethylbenzene, m-isopropylethylbenzene, p-isopropylethylbenzene may be recovered.

I claim as my invention:

1. A process for the synthesis of an alkylaromatic compound which comprises reacting an aromatic compound with a mixture of hydrogen and carbon monoxide at reaction conditions in the presence of a catalyst system comprising (1) a composite of oxides of copper, zinc and aluminum or chromium and (2) an aluminosilicate, and recovering the resultant alkylaromatic compound.

2. The process as set forth in claim 1 in which said reaction conditions include a temperature within the range of about 200° to about 400° C. and a pressure in the range of from about 1 to about 200 atmospheres.

3. The process as set forth in claim 1 in which said aluminosilicates are in crystalline or amorphous form.

4. The process as set forth in claim 1 in which said composite of oxides contains a metal of Group IA of the Periodic Table.

5. The process as set forth in claim 4 in which said metal is potassium.

6. The process as set forth in claim 1 in which said composite of oxides contains boron.

7. The process as set forth in claim 1 in which the ratio of aluminum to silicon in said aluminosilicate is greater than 2:1.

8. The process as set forth in claim 1 in which said catalyst system comprises an admixture of said composite and said aluminosilicate.

9. The process as set forth in claim 1 in which said catalyst system comprises a homogeneous mixture of said composite and said aluminosilicate.

10. The process as set forth in claim 1 in which said catalyst system comprises separate layers of said composite and said aluminosilicate.

11. The process as set forth in claim 1 in which the mole ratio of hydrogen to carbon monoxide in said reaction is in a range of from about 1:1 to about 5:1 moles of hydrogen per mole of carbon monoxide.

12. The process as set forth in claim 1 in which said mixture of hydrogen and carbon monoxide contains carbon dioxide in a range of from about 0.01:1 to about 1:1 moles of carbon dioxide per mole of carbon monoxide.

13. The process as set forth in claim 1 in which said composite contains the oxides of copper, zinc and aluminum.

14. The process as set forth in claim 1 in which said composite contains the oxides of copper, zinc and chromium.

15. The process as set forth in claim 1 in which said aromatic compound comprises benzene and said alkylaromatic compound is a mixture comprising toluene, ethylbenzene, p-xylene, m-xylene, o-xylene and cumene.

16. The process as set forth in claim 1 in which said aromatic compound comprises toluene and said alkylaromatic compound is a mixture comprising p-xylene, m-xylene, o-xylene, p-ethyltoluene, m-ethyltoluene, o-ethyltoluene, p-isopropyltoluene, m-isopropyltoluene, o-isopropyltoluene.

* * * * *